US008140267B2

(12) United States Patent
Boyer et al.

(10) Patent No.: US 8,140,267 B2
(45) Date of Patent: Mar. 20, 2012

(54) SYSTEM AND METHOD FOR IDENTIFYING SIMILAR MOLECULES

(75) Inventors: Stephen Kane Boyer, San Jose, CA (US); Gregory Breyta, San Jose, CA (US); Tapas Kanungo, San Jose, CA (US); Jeffrey Thomas Kreulen, San Jose, CA (US); James J. Rhodes, Los Gatos, CA (US)

(73) Assignee: International Business Machines Corporation, Armonk, NY (US)

( * ) Notice: Subject to any disclaimer, the term of this patent is extended or adjusted under 35 U.S.C. 154(b) by 1664 days.

(21) Appl. No.: 11/428,147

(22) Filed: Jun. 30, 2006

(65) Prior Publication Data

US 2008/0004810 A1 Jan. 3, 2008

(51) Int. Cl.
*G01N 33/48* (2006.01)
*G01N 33/50* (2006.01)
*G06F 17/50* (2006.01)
(52) U.S. Cl. ............................................ 702/19; 703/1
(58) Field of Classification Search ........................ None
See application file for complete search history.

(56) References Cited

U.S. PATENT DOCUMENTS

| | | | |
|---|---|---|---|
| 4,811,217 A | 3/1989 | Tokizane et al. | |
| 5,157,736 A | 10/1992 | Boyer et al. | |
| 5,418,951 A | 5/1995 | Damashek | |
| 5,647,058 A * | 7/1997 | Agrawal et al. ........................ | 1/1 |
| 5,752,051 A | 5/1998 | Cohen | |
| 5,845,049 A | 12/1998 | Wu | |
| 5,949,961 A | 9/1999 | Sharman | |
| 5,970,453 A | 10/1999 | Sharman | |
| 5,983,180 A | 11/1999 | Robinson | |
| 6,047,251 A | 4/2000 | Pon et al. | |
| 6,098,035 A | 8/2000 | Yamamoto et al. | |
| 6,167,398 A | 12/2000 | Wyard et al. | |
| 6,169,969 B1 | 1/2001 | Cohen | |
| 6,178,396 B1 | 1/2001 | Ushioda | |
| 6,189,002 B1 * | 2/2001 | Roitblat ................................ | 1/1 |
| 6,236,768 B1 * | 5/2001 | Rhodes et al. ................. | 382/306 |
| 6,311,152 B1 | 10/2001 | Bai et al. | |
| 6,314,399 B1 | 11/2001 | Deligne et al. | |
| 6,332,138 B1 | 12/2001 | Hull et al. | |
| 6,415,248 B1 | 7/2002 | Bangalore et al. | |
| 6,542,903 B2 | 4/2003 | Hull et al. | |
| 6,574,597 B1 | 6/2003 | Mohri et al. | |
| 6,636,636 B1 | 10/2003 | Takasu | |
| 6,785,651 B1 | 8/2004 | Wang | |
| 6,865,528 B1 | 3/2005 | Huang et al. | |
| 7,013,264 B2 | 3/2006 | Dolan et al. | |
| 7,013,265 B2 | 3/2006 | Huang et al. | |
| 7,016,830 B2 | 3/2006 | Huang et al. | |
| 7,031,908 B1 | 4/2006 | Huang et al. | |
| 7,046,847 B2 | 5/2006 | Hurst et al. | |
| 7,050,964 B2 | 5/2006 | Menzes et al. | |
| 7,113,903 B1 | 9/2006 | Riccardi et al. | |
| 7,129,932 B1 | 10/2006 | Klarlund et al. | |
| 7,143,091 B2 | 11/2006 | Charnock et al. | |
| 7,171,350 B2 | 1/2007 | Lin et al. | |
| 7,200,559 B2 | 4/2007 | Wang | |
| 7,206,735 B2 | 4/2007 | Menezes et al. | |
| 7,260,568 B2 | 8/2007 | Zhang et al. | |
| 7,286,978 B2 | 10/2007 | Huang et al. | |
| 7,321,854 B2 | 1/2008 | Sharma et al. | |
| 7,340,388 B2 | 3/2008 | Soricut et al. | |
| 7,343,624 B1 | 3/2008 | Rihn et al. | |
| 7,346,507 B1 | 3/2008 | Natarajan et al. | |
| 7,373,291 B2 | 5/2008 | Garst | |
| 7,398,211 B2 | 7/2008 | Wang | |
| 7,421,418 B2 | 9/2008 | Nakano | |
| 7,493,293 B2 | 2/2009 | Kanungo et al. | |
| 7,558,774 B1 | 7/2009 | Nakano | |
| 7,707,206 B2 * | 4/2010 | Encina et al. ................. | 707/716 |
| 2002/0087508 A1 * | 7/2002 | Hull et al. ......................... | 707/1 |
| 2002/0099536 A1 | 7/2002 | Bordner et al. | |
| 2003/0195890 A1 | 10/2003 | Oommen | |
| 2004/0042667 A1 | 3/2004 | Lee et al. | |
| 2004/0044952 A1 | 3/2004 | Jiang et al. | |
| 2004/0143574 A1 | 7/2004 | Nakamura et al. | |
| 2004/0176915 A1 | 9/2004 | Williams et al. | |
| 2005/0013507 A1 * | 1/2005 | Lee et al. ....................... | 382/284 |
| 2005/0203898 A1 | 9/2005 | Boyer et al. | |
| 2005/0246316 A1 * | 11/2005 | Lawson et al. ..................... | 707/2 |
| 2007/0143322 A1 * | 6/2007 | Kothari et al. ................. | 707/101 |

OTHER PUBLICATIONS

U. Bandara et al., "Fast Algorithm for evaluating word sequence statistics in large text corpora by small computers", IBM Technical Disclosure Bulletin, vol. 32, No. 10B, Mar. 1990, pp. 268-270.
R. Kubota, "Lessening Index file for full text search", IBM Technical Disclosure Bulletin, vol. 38, No. 11, Nov. 1995, p. 321.
"OpenEye Scientific Software", http://www.eyesopen.com/products/toolkits/ogham.html, 2 pages, Jun. 28, 2006.
"ACD/Name to Structure Batch", http://www.acdlabs.com/products/name_lab/rename/batch.html, 2 pages, Jun. 28, 2006.
J. Brecher, "Name=Struct: A Practical Approach to the Sorry State of Real-Life Chemical Nomenclature", J. Chem. Inf. Comput. Sci., vol. 39, 1999, pp. 943-950.
"Unofficial InChl FAQ", http://wwmm.ch.cam.ac.uk/inchifaq/, 3 pages, Jun. 26, 2006.
"Distributed Structure-Searchable Toxicity (DSSTox) Public Database Network", U.S. Environmental Protection Agency, http://www.epa.gov/ncct/dsstox/MoreonInChl.html., 4 pages, Jun. 26, 2006.
D. Weininger, "SMILES, a Chemical Language and Information System. 1. Introduction to Methodology and Encoding Rules", J. Chem. Inf. Comput. Sci., vol. 28, 1988, pp. 31-36.

(Continued)

*Primary Examiner* — Jason Sims
(74) *Attorney, Agent, or Firm* — Daniel E. Johnson

(57) ABSTRACT

A vectorization process is employed in which chemical identifier strings are converted into respective vectors. These vectors may then be searched to identify molecules that are identical or similar to each other. The dimensions of the vector space can be defined by sequences of symbols that make up the chemical identifier strings. The International Chemical Identifier (InChI) string defined by the International Union of Pure and Applied Chemistry (IUPAC) is particularly well suited for these methods.

30 Claims, 16 Drawing Sheets

OTHER PUBLICATIONS

D. Weininger et al., "SMILES. 2. Algorithm for Generation of Unique SMILES Notation", J. Chem. Inf. Comput. Sci., vol. 29, 1989, pp. 97-101.

Jia Cui et al.,"Investigating Linguistic Knowledge in a Maximum Entropy Token-Based Language Model", ASRU 2007 IEEE Workshop, Dec. 2007, pp. 171-176.

Vesa Siivola et al., "A State-Space Method for Language Modeling", ASRU 2003 IEEE Workshop, Nov. 30-Dec. 3, 2003, pp. 548-553.

Jia-Li You et al., "Improving Letter-To-Sound Conversion Performance With Automatically Generated New Words", ICASSP 2008 IEEE International Conference, Mar. 31, 2008-Apr. 4, 2008, pp. 4653-4656.

Wen Wang et al., "The Use of a Linguistically Motivated Language Model in Conversational Speech Recognition", Proceedings of IEEE International Conference on Acoustics, Speech and Signal Processing (ICASSP 2004) vol. 1, No. 17-21, May 2004, pp. I-261-I-264.

Hiroki Mori et al., "Japanese Document Recognition Based on Interpolated n-gram Model of Character", Proceedings of the Third International Conference Document on Analysis and Recognition vol. 1, No. 14-16, Aug. 1995, pp. 274-277.

Jerome R. Bellegarda et al., "A Muitispan Language Modeling Framework for Large Vocabulary Speech Recognition", IEEE Transactions on Speech and Audio Processing, vols. 6, No. 5, Sep. 1998, pp. 456-467.

Hui Mao et al., "Chinese Keyword Extraction Based on N-Gram and Word Co-occurrence", 2007 International Conference on Computational Intelligence and Security Workshops, Dec. 15-19, 2007, pp. 152-155.

Mathew Palakal et al., "A Multi-level Text Mining Method to Extract Biological Relationships", Proceedings of the IEEE Computer Society Bioinformatics Conference 2002 Aug. 14-16, 2002, pp. 97-108.

Jerome R. Bellegarda, "Exploiting Latent Semantic Information in Statistical Language Modeling", Proceedings of the IEEE vol. 88, No. 8, Aug. 2000, pp. 1279-1296.

Jen-Tzung Chien, "Association Pattern Language Modeling", IEEE Transactions on Audio, Speech and Language Processing, vol. 14, No. 5, Sep. 2006, pp. 1719-1728.

Dou Shen et al., "Text Classification Improved through Automatically Extracted Sequences", Proceedings of the 22nd International Conference on Data Engineering, Apr. 3-7, 2006, pp. 121-123.

Solen Quiniou et al.,"Statistical Language Models for On-line Handwritten Sentence Recognition", Proceedings of the 2005 Eighth International Conference on Document Analysis and Recognition, vol. 1, Aug. 29-Sep. 1, 2005, pp. 516-520.

Ave Wrigley, "Parse Tree N-Grams for Spoken Language Modelling", Grammatical Inference: Theory, Applications and Alternatives, IEEE Colloquium 1993, pp. 26/1-26/6.

P. O'Boyle et al., "Improving N-Gram Models by Incorporating Enhanced Distributions", Acoustics, Speech, and Signal Processing, ICASSP-96, Conference Proceedings 1996, IEEE International Conference Digital Object Identifier: 10.1109/ICASSP.1996.540317, Publication Year: 1996, vol. 1, pp. 168-171.

Tatsuya Kawahara et al., "Phrase Language Models for Detection and Verification-Based Speech Understanding", Automatic Speech Recognition and Understanding 1997, IEEE Workshop Digital Object Identifier: 10.1109/ASRU.1997.658977, Publication Year: 1997, pp. 49-56.

K. A. Papineni et al., "Maximum Likelihood and Discriminative Training of Direct Translation Models", Acoustics, Speech and Signal Processing, Proceedings of the 1998, IEEE International Conference Digital Object Identifier: 10.1109/ICASSP.1998.674399, Publication Year: 1998, vol. 1, pp. 189-192.

* cited by examiner a. Set n = maximum phrase size b. For i = 1 to N c. DO d. Set Counter c = 0, Entity = "".

e. WHILE c < n i. If Token[i+c] is not of interest, or is a StopWord, break ii. If (c = 0) Entity = Token[i+c]

iii. Else TmpEnity = Entity concatenated with Token[i+c]

iv. If TmpEntity is not of interest, break v. Else Entity = TmpEntity vi. Increment c f. END WHILE g. i = i + c h. END DO i. If Entity is not empty, label Entity as entity of interest.

FIG. 5

```
Context Window - k
for int i in all tokens{
   String finalToken = "";
   int j = 0;
   while (j < k) {
      String tok = getToken(i+j);
      if (isAnnotation(tok))
         if (isAnnotation(token+" " +tok)
            token = token+" " +tok;
         else
            break;
      else
         break;
   }
   i=j;
   if (finalToken != "")
      finalToken is annotation;
}
```

FIG. 6

```
                        6  6  0  0  0  0  0  0  0  0999 V2000
                        6.7092   5.6087   0.0000 C  0 0 0 0 0 0 0 0 0 0 0 0
                        6.7076   4.5056   0.0000 C  0 0 0 0 0 0 0 0 0 0 0 0
         Mole or        7.6607   3.9551   0.0000 C  0 0 0 0 0 0 0 0 0 0 0 0
         SD file:       8.6160   4.5062   0.0000 C  0 0 0 0 0 0 0 0 0 0 0 0
                        8.6121   5.6136   0.0000 C  0 0 0 0 0 0 0 0 0 0 0 0
                        7.6583   6.1591   0.0000 C  0 0 0 0 0 0 0 0 0 0 0 0
                        1  2  2  0  0  0
                        2  3  1  0  0  0
                        3  4  2  0  0  0
                        4  5  1  0  0  0
                        5  6  2  0  0  0
                        6  1  1  0  0  0
                        M  END
```

Benzene

SMILE String: c1ccccc1

InChl String: InChl = 1/C6H6/c1-2-4-6-5-3-1/h1-6H

SYSTEM AND METHOD FOR IDENTIFYING SIMILAR MOLECULES

TECHNICAL FIELD

This invention relates to a way of searching chemical structures. More particularly, the invention relates to a way of searching chemical structures having vector representations determined by the InChI and/or SMILES formats, in order to find structures having similar or identical structure.

BACKGROUND

Chemical structure representations have been evolving over the past several decades, leading to many advances in chemical informatics. Depending on the format used, chemists can quickly perform exact structure, sub-structure and similar structure queries against a collection of chemicals. Currently, there are dozens of ways to represent chemical structures for machine use. These formats vary in complexity, detail, and value. However, most chemical representations are proprietary and solutions built around them can be expensive. Some of the more common chemical file formats useful with computer analysis are SMILES (Simplified Molecular Input Line Entry System) and Connection Table Files, but the search engines employed with these formats can be difficult to work with. The IUPAC (International Union of Pure and Applied Chemistry) International Chemical Identifier (InChI) is an open system for generating unique string representations of chemical compounds, but there is currently no search engine that can directly search InChI strings ("InChIs") to determine chemical similarity.

SUMMARY OF THE INVENTION

The invention is directed to methods of performing searches on chemical structures, especially those presented in the InChI and/or SMILES formats. In addition to finding matching chemical structures, preferred methods disclosed herein enable one to search for molecules having similar structures (similarity searching), e.g., those having functionally similar molecular content. Text mining techniques are employed, and vector space models are employed for nearest neighbor calculations.

In preferred embodiments of the invention, SMILE (Simplified Molecular Input Line Entry) System chemical identifier strings or preferably InChI (International Chemical Identifier) chemical identifier strings are transformed into vectors, which are then used in a process to identify chemical structures that are similar or even identical to each other.

One aspect of the invention is a method that includes constructing a vector space having dimensions determined by a plurality of chemical identifier strings (in which the strings are determined by respective chemical compounds) and constructing a vector for each of the strings (in which each vector has the dimensions of the constructed vector space). The method may further include computing a measure of similarity between vectors, so that vectors (and their corresponding compounds) that are identical or similar to each other can be identified. To this end, the vectors may be ranked according to the computed measure of similarity. The strings are preferably InChI strings, and sparse vector representations can be used to increase computational efficiency.

Another aspect of the invention is a method that includes extracting sequences of symbols from each of a plurality of chemical identifier strings (in which each string is associated with a chemical) and defining a vector for each of the strings (in which the vectors have a common vector space that includes dimensions given by the extracted sequences). InChI strings may be used, with the extracted sequences including consecutive symbols containing carbon connectivity information and/or consecutive symbols containing hydrogen connectivity information. In addition, the vector space may include dimensions defined by information taken from chemical formulae of the chemicals, e.g., the vector space may include dimensions defined by elements of the chemical formulae. Each of the extracted sequences may advantageously have no greater than a predetermined number of symbols, and the extracted sequences may include consecutive symbols of every possible sequence up to the predetermined number of symbols. The vectors are preferably represented by respective sparse vector representations, and chemicals that are at least similar to each other may be identified by calculating a similarity value between a given vector (e.g., query vector) and each of a plurality of the defined vectors.

Yet another aspect of the invention is a method that includes converting chemical names to respective chemical identifier strings (in which the strings have a common format, such as the InChI format) and constructing respective vectors from the strings. At least some of the vectors (or even all of them) are stored in at least one memory device, and at least some (or even all) of the stored vectors are searched to identify certain chemical structures are similar (or even identical) to each other. For example, IUPAC names may be converted to respective structures, and then the respective structures may be converted to respective chemical identifier strings having the common format. The vectors are preferably normalized to unit vectors and expressed as sparse vector representations, and a vector corresponding to a query molecule may be used to identify said certain chemical structures. Since the chemical names themselves may be extracted from the text of different documents, the particular documents from which said certain chemical structures have been extracted can then be identified. If these documents include patents, the assignees and the inventors may also be identified.

Yet another aspect of the invention is a method that includes extracting chemical entities from different documents (in which the chemical entities have different formats with respect to at least one of name and chemical identifier string) and representing the chemical entities as respective chemical identifier strings having a common format. Respective vectors are constructed from the commonly formatted chemical identifier strings, with at least some (or all) of them being stored in at least one memory device. At least some of (or all) of the stored vectors may then be searched. The chemical entities may include chemical names, chemical formula, chemical structures, and chemical identifier strings. Respective vectors may be advantageously constructed by extracting sequences of symbols from each of the commonly formatted chemical identifier strings and defining a vector for each of the commonly formatted strings (in which the vectors have a common vector space that includes dimensions given by the extracted sequences). The commonly formatted strings are preferably InChI strings. However, the strings may include not only information in the InChI format, but also additional information related to functional properties of the chemical entities, and the method may further include searching on this additional information.

The methods herein lend themselves to being used with large document sets, e.g., more than one million extracted chemical names may be converted to a common string format, such as the InChI format. Chemical names may be extracted from documents in the following way: At least one document having text can be tokenized, so that tokens correspond to terms within the document. Each token is evaluated against at least 2 different Markov models to determine respective relative probabilities that the token corresponds to the Markov models (with at least one of the Markov models being directed to chemical terms) and for each token, the relative probabilities are compared with each other to determine which Markov model is more likely to be associated with the token. Tokens most likely to correspond to a Markov model directed to chemical terms are then identified, so that chemical terms within the document are identified.

In other implementations, there are provided computer program products for carrying out any of the methods herein. The computer program products may include at least one tangible computer-useable medium having a computer-readable program. Upon being processed on a computer, the program (which includes code) causes the computer to implement the various steps of the method. A computer system for carrying out the methods disclosed herein may include the aforementioned said at least one medium and a processor in communication with said at least one medium. One particular computer-implemented method may include processing the program of the aforementioned said at least one medium to implement the various steps of the method, and then delivering to a client output resulting from implementing these steps.

BRIEF DESCRIPTION OF THE DRAWINGS

FIG. 1 includes FIGS. 1A and 1B, in which:

FIG. 3 includes FIGS. 3A and 3B, in which:

FIG. 5 shows code that may be used as part of an annotation algorithm;

FIG. 6 shows code for clustering consecutive tokens found to be of the same type of text entity;

DETAILED DESCRIPTION OF THE INVENTION

Various aspects of preferred embodiments of the invention are now described in the different sections below.

1. Extracting Chemical Entities from a Corpus (or Corpora)

In preferred embodiments of the invention, similarity searching is performed on a set of chemical names, which may be generated from a corpus (or corpora) of interest. For example, the corpus in question may be all issued US patents, if that is of particular interest to the user, or the corpus may be the peer-reviewed chemical literature. Although chemical names may be extracted from source documents manually, this is generally cumbersome, and it is preferable to automate this process. One such automated process is disclosed in US Patent application publication 2005/0203898A1 to Boyer et al. titled "System and method for the indexing of organic chemical structures mined from text documents", which was published Sep. 15, 2005.

One preferred method of extracting chemical entities from patents and/or references in the scientific literature is described in commonly assigned application Ser. No. 11/421,379 filed May 31, 2006 and titled "System and method for extracting entities of interest from text using N-gram models", which is hereby incorporated by reference. That method allows the user to analyze text to identify entities of interest within that text, and is now described with respect to several of the figures herein.

Figure 1A:
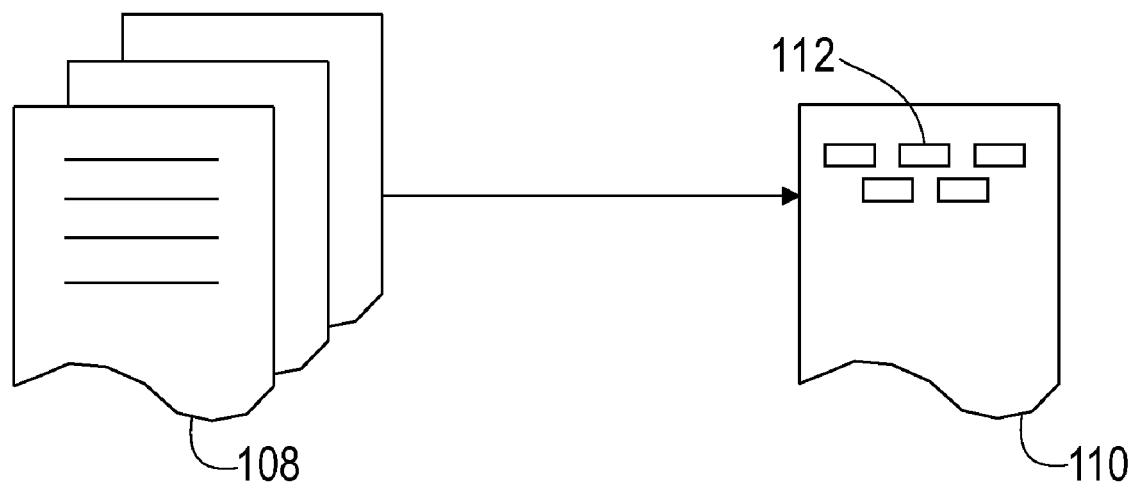
FIG. 1A shows documents being tokenized.
Figure 1B:
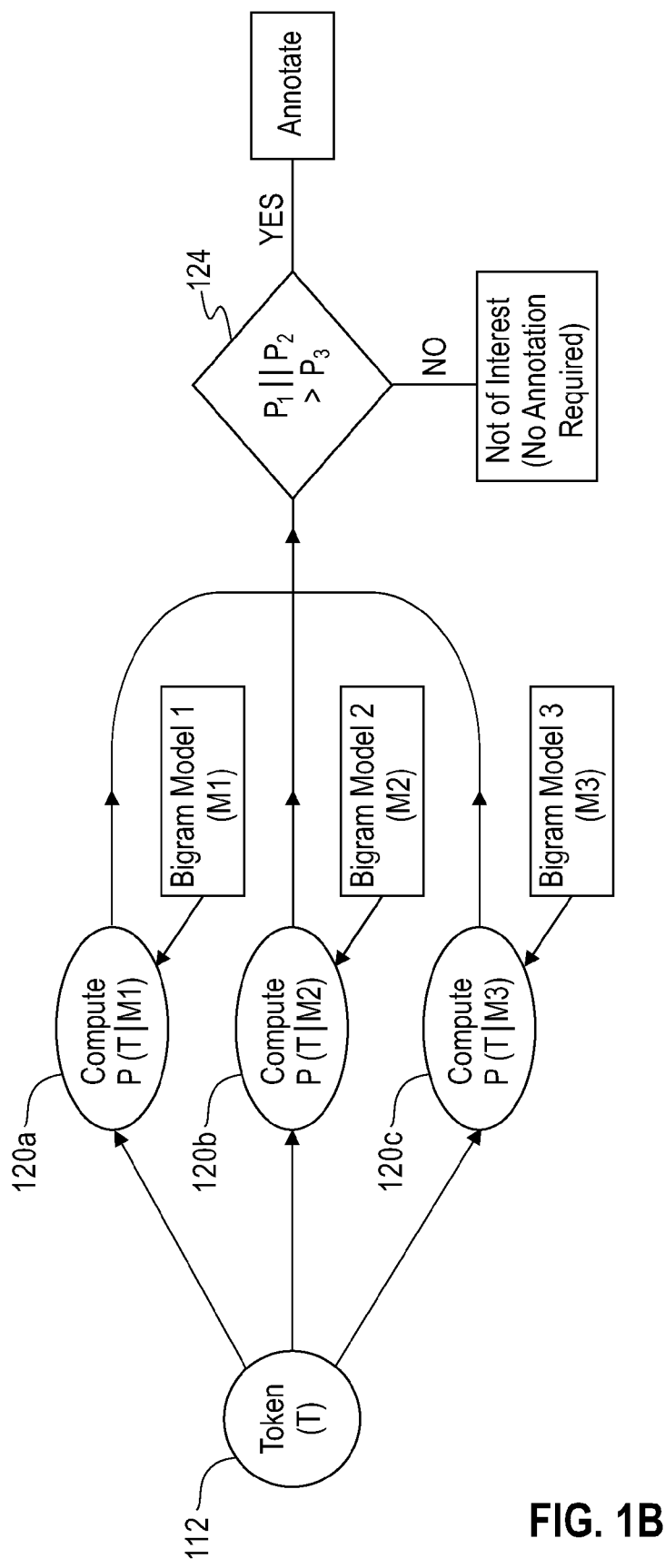
FIG. 1B shows a decision tree for determining whether to annotate a document for a given token.

FIGS. 1A and 1B show one preferred annotation technique used in identifying and extracting chemical entities of interest. As shown in FIG. 1A, text, which may be in the form of one or more documents 108 (e.g., documents that are retrievable and/or storable in electronic format), is passed through a tokenizing routine to form tokenized documents 110 that include space-delimited stings or tokens 112.

As shown in FIG. 1B, these tokens 112 are then analyzed by two (or more) models M1, M2, M3, each of which has been previously trained to recognize a different type of entity, such as a chemical name (e.g., M1), a chemical formula (e.g., M2) or a plain text English language word of no particular chemistry-related interest (e.g., M3); thus, these models are used to classify the tokens. The models M1, M2, M3 of FIG. 1B are different annotation bi-gram models, which are described in greater detail below. For each token 112 in the tokenized documents 110, the models M1, M2, M3 are used in a computation step 120a, 120b, 120c, respectively, the output of which is the corresponding name of the entity type (such as "chemical" for M1 and M2, and "not a chemical" or "English" for M3) and a probability P1, P2, P3, respectively, that the token in question corresponds to the type of entity for which the given model has been trained. A comparison 124 is then made of these probabilities P1, P2, P3. That is:

$$\text{BestModel} = \operatorname{argmax}\_\{\text{model } 1, \ldots, \text{model } N\} \text{Prob}(\text{token}|\text{model}) \quad (1)$$

Each token may then be assigned the entity name corresponding to the model giving rise to the greatest probability, i.e., the entity name is given by the entity type of BestModel. The system may then annotate the document(s) 108 and/or 110, e.g., electronically. (In the event that the greatest probability corresponds to an entity type that is not of interest, no annotation is required.) For example, a sentence like "We then add 5 ml of $H_2SO_4$ to the mixture" could be annotated as "We then add 5 ml of <chemical> $H_2SO_4$ </chemical> to the mixture." The markup can be done in various ways, such as using markup language like XML. Alternatively, "standoff" files may be generated in which the annotation information is kept separate from the document(s) 108 and 110.

As mentioned above, each model M1, M2, M3 is designed to recognize a particular type of entity. To this end, statistical bi-gram language models have been found to work well. In general n-gram models (in which n is the number of consecutive characters analyzed and is greater than two) may be used, although the amount of training data required increases rapidly with n. The training process requires sample entities (e.g., words, terms, phrases, formulae) for each type of entity (chemical name, English language word, etc.) that a user wants to recognize. Once this training collection is in hand, it is used to build an associated bi-gram language model.

Figure 2:
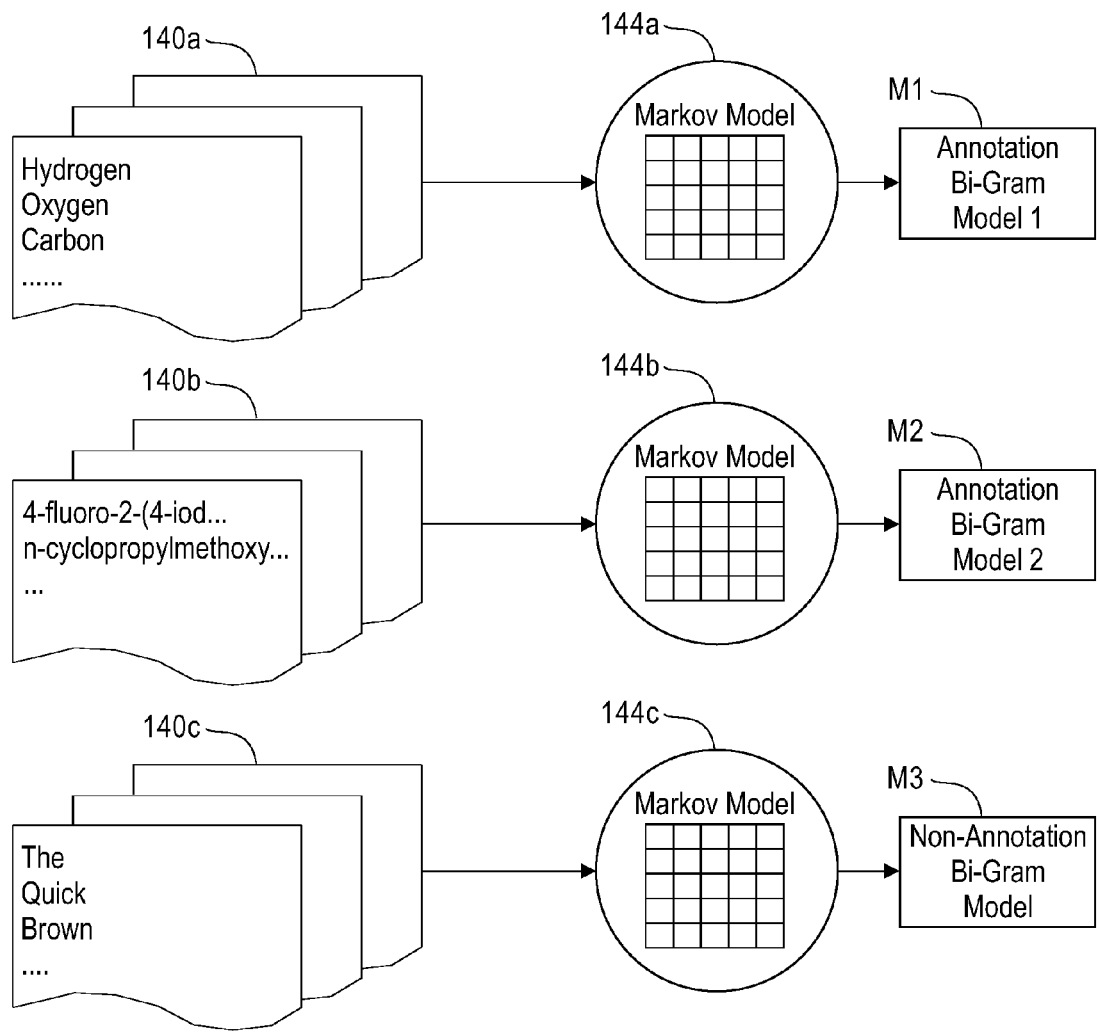
FIG. 2 shows training text being used to train the bi-gram models of FIG. 1B, in which the bi-gram models correspond to different types of text entities.

This training procedure is shown in FIG. 2. A collection of terms 140*a* consisting of chemical names (prose) is run through a Markov model 144*a* to form a first (annotation) bi-gram model M1. Likewise, a collection of terms 140*b* consisting of chemical names (formulae) is run through a Markov model 144*b* to form a second (annotation) bi-gram model M2. In addition, a collection of terms 140*c* consisting of words of the English language is run through a Markov model 144*c* to form a (non-annotation) bi-gram model M3. Each of the document collections 140*a*, 140*b*, 140*c* used as the training sets should be representative of the corpus for which the model M1, M2, M3 will be used.

If a chemical model and a model directed to non-chemical terms are used, the non-chemical model is preferably trained with text that does not include any chemically related terms, phrases, and formulae. (Text having a few chemically related terms, phrases, and formulae may be used with less favorable results.) In general, training text can be i) manually created, ii) acquired from various existing sources like general usage or specialty dictionaries, or iii) systematically generated by parsing unstructured text, creating phrases, and then using an algorithm that tests that fragments are arranged according to some pre-specified rule characterizing the entities of interest.

Figure 3A:
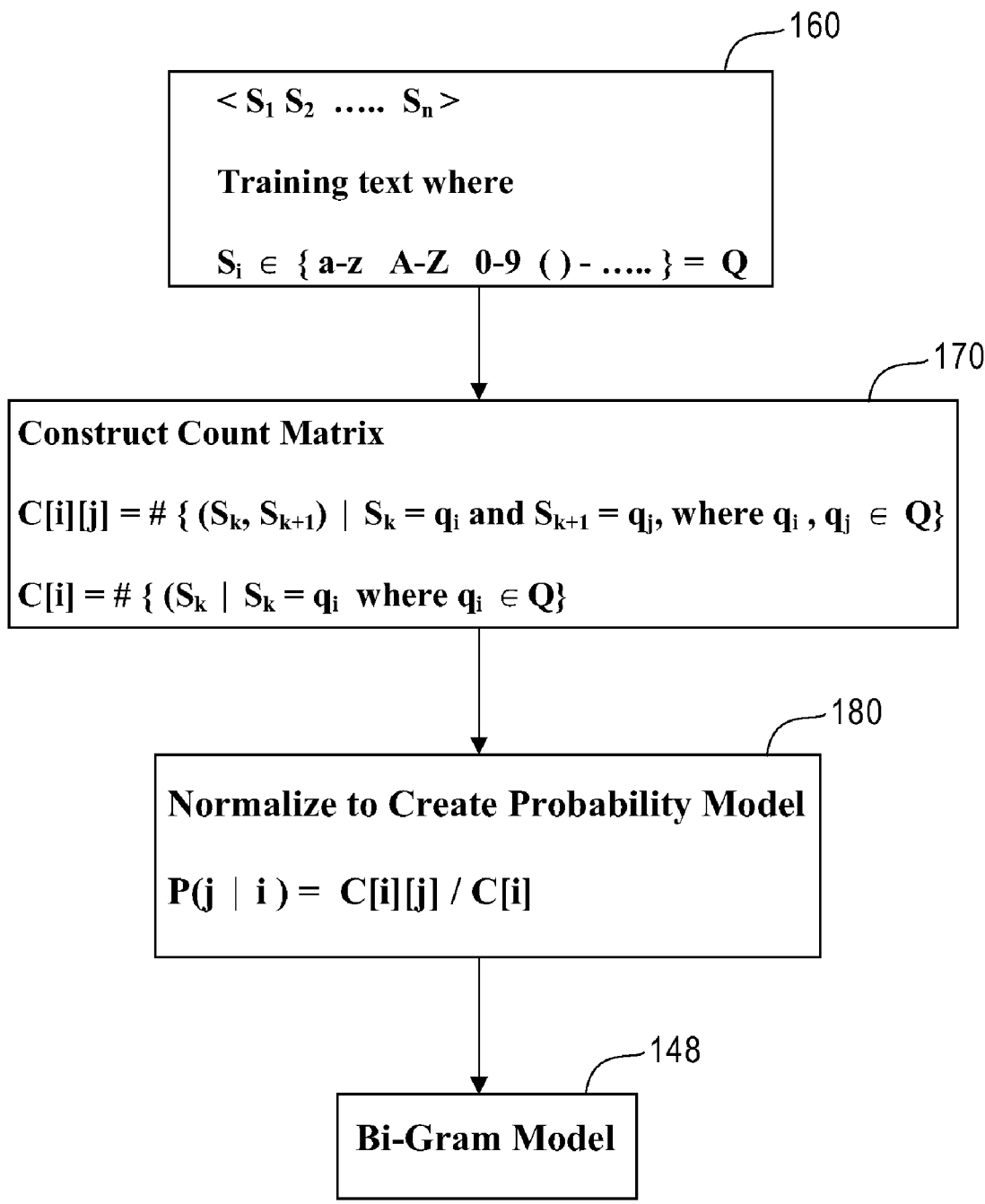
FIG. 3A shows how a bi-gram model is constructed from training text.
Figure 3B:
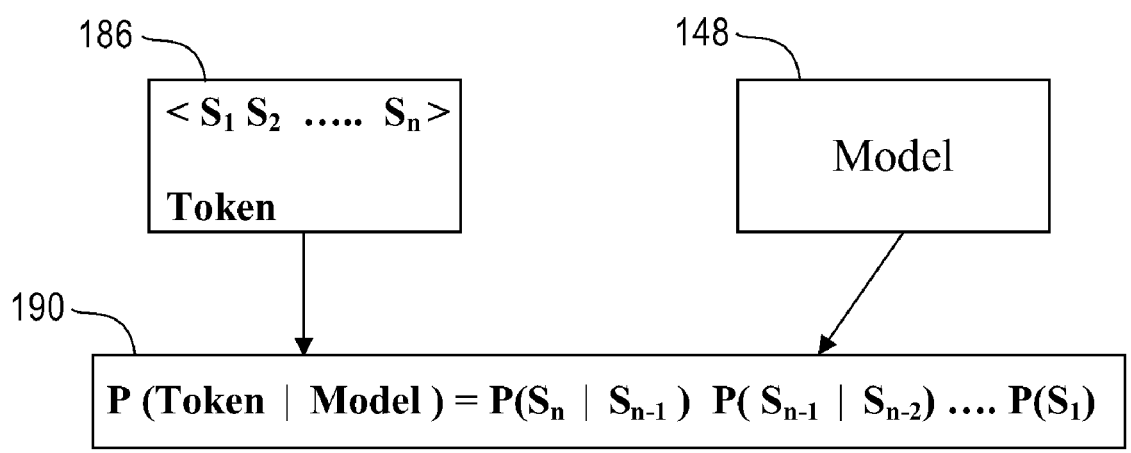
FIG. 3B shows how to calculate the probability that a given token is of a particular type of text entity.

Preferred ways of constructing a bi-gram probability model are now described in greater detail with respect to FIGS. 3A and 3B. FIG. 3A outlines a process by which a bi-gram language model is created. This process uses first order Markov assumptions (see, for example, Papoulis and Pillai, "Probability, Random Variables, and Stochastic Processes," McGraw Hill, 2001). The process begins with a collection of terms (140*a*, 140*b*, or 140*c*) having its own alpha-numeric and/or other text-based symbols $s_I$, which may also include prefixes and suffixes (see step 160 of FIG. 3A). An assumption is made that the probability of observing a particular sequence of symbols $s_1, s_2, \ldots, s_N$, each of which is found in the corresponding collection of terms (140*a*, 140*b*, or 140*c*), is given by $$P(s_1, s_2, \ldots, s_N | \text{model}) = P(s_N | s_{N-1}) * P(s_{N-1} | s_{N-2}) * \ldots * P(s_2 | s_1) * P(s_1) \quad (2)$$

The individual conditional probabilities in the products $P(s_I | s_{I-1})$ can be estimated from the collection of terms (140*a*, 140*b*, or 140*c*) by counting the number of times that $s_I$ immediately follows $s_{I-1}$ (step 170), and then normalizing this number by the total number of times $s_{I-1}$ appears in the collection of terms in question (step 180). The result is a bi-gram model 148, such as M1, M2, and M3. Thus, the bi-gram models M1, M2, M3 are concerned with the probability of transitioning from one symbol to another. Accordingly, the models M1, M2, M3 can each be represented using a matrix in which each cell of the matrix gives the transition probability for observing the symbol $s_I$ followed by the symbol $s_2$. That is, an individual cell $C[i][j]$ of a count matrix essentially records the number of times the symbol $S_i$ was immediately followed by the symbol $S_j$ in the training corpus (see step 170). If one then divides this quantity by the number of times $C[i]$ that the symbol $S_i$ occurred in the corpus (see step 180), one gets an estimate of the conditional probability: $P(j|i) = C[i][j]/C[i]$.

FIG. 3B shows how once these probabilities are estimated for a particular type of entity in accordance with a certain model 148, one can compute the probability that a given token 186 is the same type of entity by multiplying together all the terms in equation (2), shown as step 190. Note that while the true probabilities and conditional probabilities are not known, these can be estimated from the documents 108 and/or 110 by counting the number of relative number of occurrences of the specific pattern in which one is interested, compared to all the unique patterns that occurred in the documents.

Figure 4:
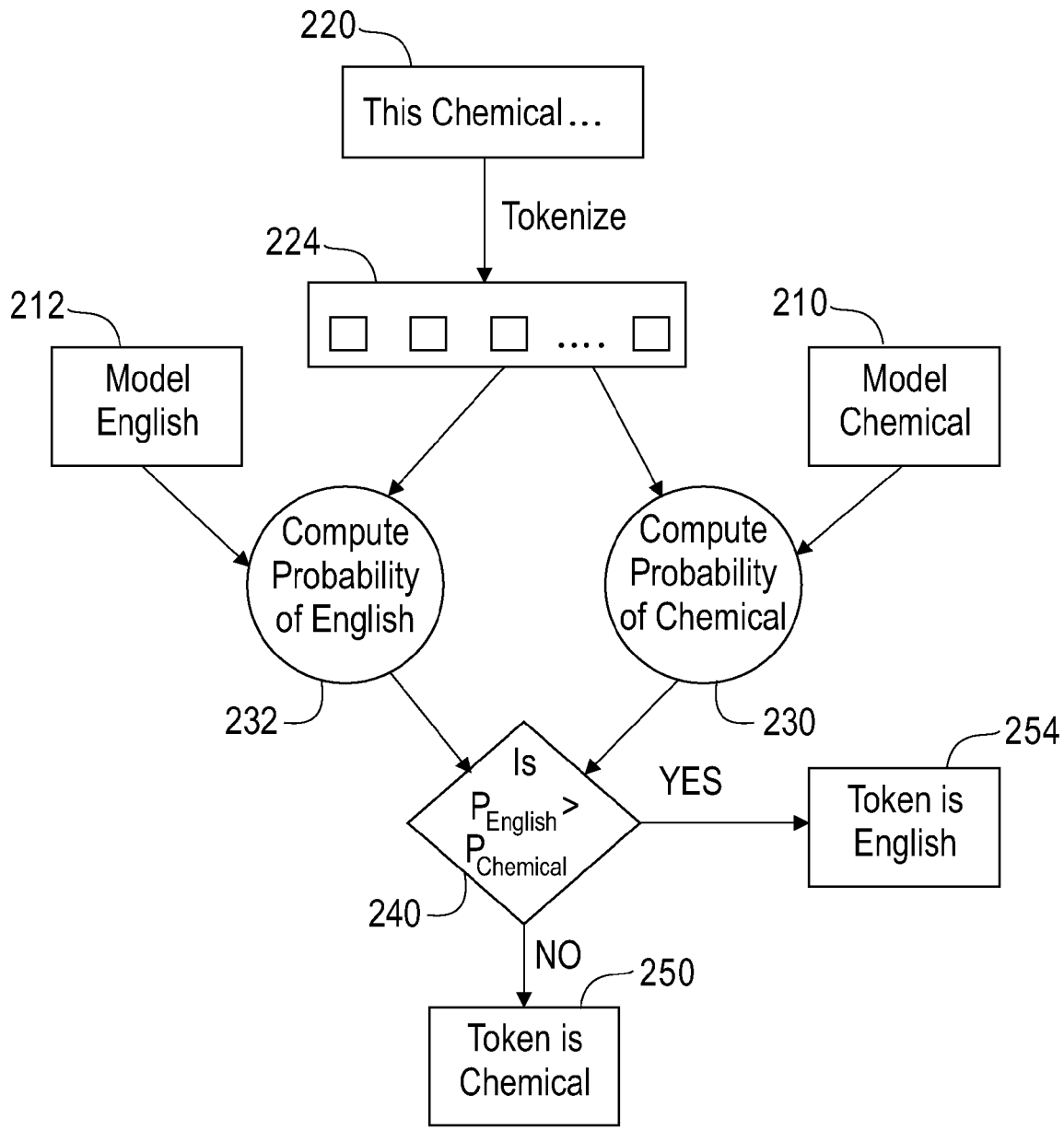
FIG. 4 shows a tokenization process and a decision tree for determining whether to annotate an entity in a document.

With respect to FIG. 4, consider once again the problem of finding chemical entities in a document. The document could be, for example, a US patent that discloses certain chemical drugs. In this case, the user will want to find text corresponding to chemical entities. In this example, one employs two models 210 and 212, which are directed to chemical names/formulae and general usage, plain text (non-chemical) English words, respectively. The English language model 212 is preferably trained with text having no or few chemical names (e.g., such as general interest articles from a newspaper). The chemical model 210 can be trained on a database of chemical names.

Given a text string 220 from which is constructed a set 224 of tokens, the chemical model 210 and the English language model 212 are then used to compute the probabilities that each token is a chemical name or a general usage English word (steps 230, 232, respectively). These probabilities are compared (step 240): If the chemical model 210 assigns a greater probability to the token than the English language model 212, the token is denoted and annotated as being chemical (step 250); otherwise, the token is denoted as being English or not-a-chemical (step 254). This process is then repeated for all tokens in the document(s) of interest. The document(s) may then be annotated to indicate which terms, phrases, formulae, etc. are chemical in nature. FIG. 5 shows code that may be used as part of an annotation algorithm.

FIG. 6 shows code that may be used as part of a grouping step. That is to say, if consecutive tokens are found to be of the same type of entity, they may be advantageously clustered together and the maximal token sequence is assigned the associated entity type. While individual tokens can be chemical entities, multiple consecutive entities may at times form a specific chemical token. That is, the contiguous set of tokens taken together can be viewed symbolically as forming one chemical entity. The code shown in FIG. 6 essentially collects neighboring tokens that have been identified as belonging to one entity type, and then groups and labels them as one token.

Once the chemical terms of interest have been identified, they may be extracted from their respective source document(s) and stored in a database. Such a database advantageously indexes the extracted chemical terms against their respective source documents.

2. Chemical Identifier String Formats

Figure 7:
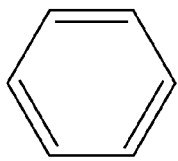
FIG. 7 shows how a molecule can be represented in variety of different chemical identifier formats.

A number of chemical identifier formats are commonly used, such as the various connection table formats, which describe in detail the structural relationships between the atoms that form a given molecule. Some file types that leverage connection tables are the MOLfile for a single (multifragment) molecule, the RGfile for a generic query, the SDfile for multiple structures and data, the RXNfile for a single reaction, and the RDfile for multiple reactions and data. A connection table typically includes a counts line, an atom block, a bond block, an atom list block, and a block of properties. One example of a connection table is shown in FIG. 7 for the molecule benzene. Unfortunately, for all but the simplest molecules, the large amount of data in connection tables can make them difficult to work with. In any case, they can not be used directly with the methods disclosed herein.

In preferred embodiments of the invention, SMILE (Simplified Molecular Input Line Entry) System chemical identifier strings or preferably InChI (International Chemical Identifier) chemical identifier strings are transformed into vectors, which are then used in a process to identify chemical structures that are similar or even identical to each other. The SMILE System is a chemical notation system designed for modern chemical information processing (see, for example, D. Weininger, "SMILES, a chemical language and information system. 1. Introduction to methodology and encoding rules", J. Chem. Inf. Comput. Sci. v. 28, pp. 31-36, 1988). With this system, a compact string representation of a molecule is employed that is based on molecular graph theory (see, for example, the web site identified by the concatenation of "www." and "daylight." and "com/smiles/index.html"). Rather than using a computer data structure or a mathematical abstraction, the SMILE System uses a valence model of a molecule, which treats a molecule as being composed of constituent atoms and bonds (see, for example, D. Weininger, A. Weininger, J. L. Weininger, "Algorithm for Generation of Unique SMILES Notation", J. Chem. Inf. Comput. Sci. v. 29, pp. 97-101, 1989).

FIG. 7 shows a SMILES string for the compound benzene. The simple, compact representation of the SMILES strings makes this system useful for searching large databases of chemical structures. However, one problem with the SMILE System nomenclature is that the same molecule may have different SMILES representations, since different algorithms may be used to generate a representation. Although a canonical SMILE System can guarantee that the resulting string for a particular compound is unique, there may be different algorithms that generate different canonical SMILES strings.

InChIs are open source chemical identifiers developed under the auspices of the International Union of Pure and Applied Chemistry (IUPAC). They lend themselves to both printed and electronic data formats. For a given molecule, an InChI is established using a three step process related to chemistry, math, and formatting. In the chemistry-related step, a compound is normalized by applying chemical rules. The math-related step involves 'canonicalizing' (labeling the atoms) and ensuring that equivalent atoms are assigned the same label. The formatting step involves serializing and generating a unique name. As is evident from FIG. 7, and as discussed in greater detail below with respect to FIG. 8, the InChI format consists of multiple "layers", thereby allowing detailed information to be compactly represented. Because any given molecule has a unique InChI, it is the preferred kind of chemical identifier for use with the methods disclosed herein. Information on the InChI chemical identifier format is available from IUPAC and various web sites, such as the one whose address is given by the concatenation of "wwmm" and "ch.cam.ac.uk/inchifaq/".

Figure 8:
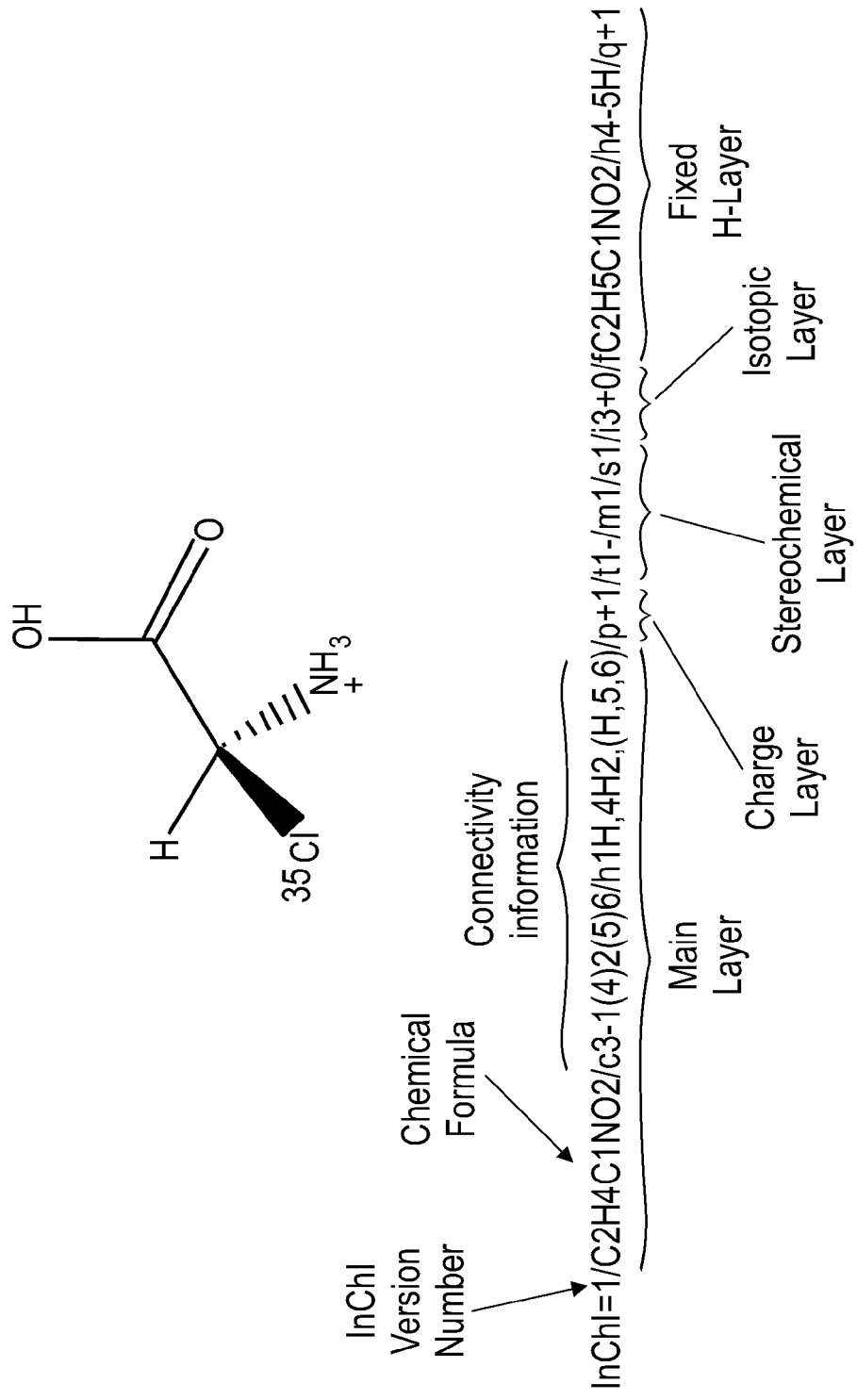
FIG. 8 gives the InChI chemical identifier format of the indicated chemical.

FIG. 8 illustrates in greater detail an InChI chemical identifier string, in particular, the InChI string for the molecule 1-chloro-1-nitro-ethane. The numeral "1" in this string represents the InChI version number, which is followed by a number of layers and sub-layers separated by the forward slash symbol "/". The main layer includes a sub-layer for the molecule's chemical formula, which in this case is C2H4ClNO2. An InChI's main layer may further include a sub-layer for connectivity information (excluding terminal hydrogen), which begins with the letter "c" and generally includes carbon connectivity information if carbon is present; this sub-layer is also referred to as the "connectivity-1.1" sub-layer. This connectivity sub-layer may in turn be followed by a hydrogen connectivity sub-layer, which begins with the letter "h"; this sub-layer, also known as the "connectivity-1.2" sub-layer, gives the locations of terminal hydrogen atoms, including mobile hydrogen attachment points.

As shown in FIG. 8, various other layers follow the main layer, assuming they are present at all. The charge layer or proton balance layer is next. It is followed by the stereochemical layer, which includes sub-layers beginning with "t" (which indicates the tetrahedral parity of the molecule), "m" (which indicates the parity inverted to obtain relative stereo, in which "1" means inverted, "0" means not inverted, and "." means unaffected by inversion), and "s" (which indicates the stereo type, in which "1" means absolute, "2" means relative", and "3" means racemic). The stereochemical layer is followed by the isotopic layer, which begins with the letter "i". This is followed by the fixed H-layer, which includes sub-layers beginning with the letter "f" (which gives the chemical formula of the fixed H-structure if this is different from the chemical formula in the main layer), "h" (also known as the "connectivity-2" layer, which gives the locations of the fixed mobile hydrogen), and "q" (which gives the charge of the fixed H-structure). Still other layers may follow the layers discussed above to define various other structural aspects of a particular molecule. By convention, all these layers and their sub-layers are always presented in a predefined order, consistent with the InChI strings shown in FIGS. 7 and 8, although depending on the molecule certain sub-layers and/or layers may not be included in the string. Furthermore, only part of an InChI string may be used to at least partially define a molecule by truncating the string after a certain layer or sub-layer.

3. Converting Extracted Chemical Entities to InChI or SMILES Strings

Stand-alone chemical entities (such as chemical names) extracted from the corpus are first transformed into either a SMILES or InChI chemical identifier string (which is then vectorized, as discussed below). This transformation may include feeding chemical names (e.g., the corresponding IUPAC names) through a name-to-structure program that generates respective connection tables for the chemical names. These connection tables may then be converted into InChI strings using openly available InChI code. For example, several organizations provide free and open access to programs that allow one to convert Structure Data (SD) files and/or SMILES strings into InChI file formats (e.g., see the Environmental Protection Agency website whose address is given by the concatenation of "www." and "epa." and "gov/ncct/dsstox/MoreonInChI.html"). Alternatively, the connection tables (e.g., SD file or Mole-file) may be converted into a (preferably canonical) SMILES string by commercial software applications such as those offered by CambridgeSoft Corporation (Cambridge, Mass., USA and Cambridge, United Kingdom) and Advanced Chemistry Development Labs (ACD Labs, Toronto, Ontario, Canada).

More generally, all the chemical entities from the corpus' various documents, whether they be chemical names written as prose (e.g., IUPAC names or names given by other conventions), chemical formula, chemical structures, or chemical identifier strings, may be extracted from these documents and then expressed as respective chemical identifier strings having the same format. Thus, if necessary, certain ones of the chemical names and/or entities identified in the corpus of interest are converted to a pre-selected chemical identifier string format, with the result being that the user has a collection of either InChI or SMILES strings corresponding to all the chemicals identified in the corpus. This is indicated step 300 in FIG. 9. By representing all the chemical names by a common kind of chemical identifier string, the similarity searching described below is facilitated.

If the chemical corpus (or corpora) of Section 1 includes SMILES and/or InChI strings, those strings may be extracted from the corpus along with other chemical entities of interest. Since it is preferable that this common representation be in the InChI format, it is desirable to convert any SMILES strings found in the corpus to an InChI string first by, for example, running the SMILES to InChI conversion programs discussed above. Alternatively, but less desirably, all InChI strings may be converted into the SMILES format by available software applications (such as those from Cambridgesoft Corporation or ACD software).

4. Constructing Vectors from InChI or SMILES Strings

Once the collection of InChI or SMILES strings from Section 3 is in hand, vectors are constructed from these strings (step 310 of FIG. 9) so that similarity searching can be performed. A preferred way of vectorizing these strings is explained with respect to the examples presented below.

A. Constructing Vectors from InChI Strings

Consider the following two InChI strings corresponding to water and nitrous oxide, respectively:
1/H2O/h1H2 and
1/N2O/c1-2-3.

Note that in the case of water, the only connectivity sub-layer in the main layer of its InChI string is directed to hydrogen. On the other hand, nitrous oxide has no hydrogen, so its InChI string has no hydrogen connectivity sub-layer but does have a connectivity sub-layer (that is unrelated to hydrogen or carbon, which is not present in nitrous oxide). Thus, in this particular example, each of the main layers includes only one sub-layer (in addition to the chemical formula sub-layer, which is present in any InChI string). Each of these two connectivity sub-layers may be regarded as a collection of symbols that follow the letter identifying that sub-layer: "1H2" in the case of water (which follows the letter h) and "1-2-3" in the case of nitrous oxide (which follows the letter c).

The process of forming a vector space may include extracting from each sub-layer's collection of symbols every possible substring or sequence of symbols in that collection. For example, in the case of water, the possible sequences include the following: 1, 1H, 1H2, H, H2, and 2. In the case of nitrous oxide, the unique sequences include the following: 1,1-, 1-2, 1-2-, 1-2-3, -, -2, -2-, -2-3, 2, 2-, 2-3, -3, and 3. As a practical matter, it is advantageous to identify only those sequences having a maximum length n, e.g., sequences up to 3 symbols in length, since otherwise the vectorization process can become too complicated. If this simplification is invoked and n is selected to be 3, then the set of sequences for nitrous oxide is somewhat smaller and only includes 1, 1-, 1-2, -, -2, -2-, 2,2-, 2-3, -3, and 3 (i.e., only those sequences having three or fewer symbols). However, if n is too small, the resulting vector space may be too small to perform good similarity searching.

In addition to identifying sequences of symbols in the connectivity sub-layers, sequences of symbols from the chemical formula sub-layer can be extracted as well. In the case of water (H2O), for example, these sequences would include the following: H, H2, H2O, 2, 2O and O. With respect to the chemical formula sub-layer, however, it has been found preferable to extract just the symbols representing the individual elements (rather than every possible sequence of symbols) along with the number of times those elements are found in the corresponding chemical compound. For example, water is composed of O (1 atom) and H (2 atoms), and nitrous oxide is composed of O (1 atom) and N (2 atoms).

In view of the forgoing, the dimensions of a vector space defined by the compounds water and nitrous oxide may be determined by:

a) extracting only elements and their frequencies of occurrence from the chemical formula sub-layer (as opposed to extracting multi-symbol sequences, which may be done in alternative embodiments of the invention);

b) extracting only sequences having up to 3 symbols from the connectivity sub-layers (i.e., n=3, although in alternative embodiments of the invention n may be chosen differently); and c) adding prefixes to the sequences identified in b) using letters that identify where the sequences originate, e.g., any sequence of symbols originating from the connectivity sub-layer includes the letter c, and any sequence originating from the hydrogen connectivity sub-layer includes the prefix h. The reason for step c) is that it allows one to disambiguate sequences from different layers or sub-layers that would otherwise be identical. (Alternatively, one may add suffixes to the sequences, or more generally insert "tags" somewhere in the sequences.)

Accordingly, such a vector space constructed from the water and nitrous oxide InChI strings includes the following unique dimensions:

H, O, h1, h1H, h1H2, hH, hH2, h2, N, c1, c1-, c1-2, c-, c-2, c-2-, c2, c2-, c2-3, c-3, c3.

The corresponding vectors for this vector space are
{2,1,1,1,1,1,1,1,0,0,0,0,0,0,0,0,0,0,0,0} for water, and
{0,1,0,0,0,0,0,0,2,1,1,1,2,1,1,1,1,1,1,1} for nitrous oxide.
Note that the "H-dimension" of the vector for water is assigned a value of 2, because water has 2 hydrogen atoms. Likewise, the "N-dimension" of the vector for nitrous oxide is assigned a value of 2. In addition, there are two instances of the symbol "-" in the connectivity layer of nitrous oxide, so the value of the corresponding dimension in the nitrous oxide vector is also 2. The value of each of the other dimensions in these two vectors is either 1 or 0, as appropriate, and for a given vector is equal to the number of times the corresponding sequence is found.

Note that this vector construction methodology can be extended to include other layers and sub-layers, such as those described in connection with FIG. 8. Also, it should be noted that the vector space itself generally depends on the number of InChI strings under consideration. For example, constructing a vector space from water, nitrous oxide, and benzene strings would involve dimensions in addition to those already considered, since sequences of symbols can be extracted from benzene's InChI string that are not found in either water or nitrous oxide. Thus, the number of dimensions in the constructed vector generally increases as additional molecules are considered. For this reason, it may be advantageous to limit n to a relatively small number, as noted in b) above. Likewise, sparse representations of the vectors are preferred in order to improve computational efficiency and optimize performance. For example, sparse representations of the vectors presented above are:
<2,(7,1),(12,0)> for water, and
<0,1,(6,0),2,(3,1),2,(7,1)> for nitrous oxide.

B. Constructing Vectors from SMILES Strings

The SMILES representations of the molecules just considered, water and nitrous oxide, are:
[H]O[H] and
O=N#N.
Vectors may be constructed from SMILES strings in a way that is in some respects analogous to the procedure described above with respect to InChI strings. First, sequences of symbols from these strings are extracted. The extracted sequences may include any possible sequence of symbols or, for example, only those sequences having up to a certain number of consecutive symbols may be identified. In the latter case, if n is selected to be 3, then the set of unique extracted sequences for the two molecules in question is
[, [H, [H], H, H], H]O, ], ]O, ]O[, O, O[, O[H, O=, O=N, =, =N, =N#, N, N#, N#N, #, #N
and the corresponding vectors having these dimensions are {2,2,2,2,2,1,2,1,1,1,1,1,0,0,0,0,0,0,0,0,0} for water; and {0,0,0,0,0,0,0,0,0,1,0,0,0,1,1,1,1,2,1,1,1,1} for nitrous oxide.
Note that the value of each dimension corresponds to the number of times the sequence in question is found in the corresponding SMILES representation.

C. Vector Normalization

Figure 9:
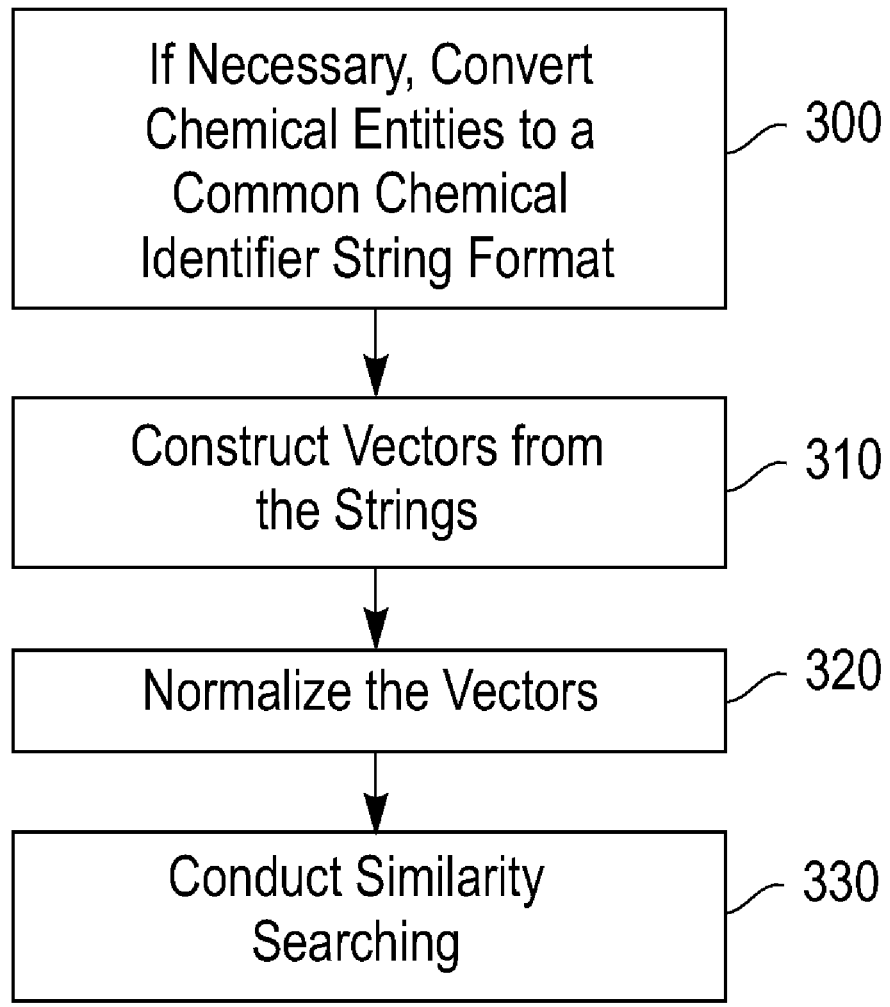
FIG. 9 gives an overview of a preferred method for conducting similarity searching on chemicals.

Once vectors have been constructed from the various chemical identifier strings (either InChI or SMILES) under consideration, these vectors are preferably normalized, as indicated by step 320 of FIG. 9. This vector normalization facilitates better similarity searching, which is discussed in the next section.

5. Similarity Searching

Figure 10:
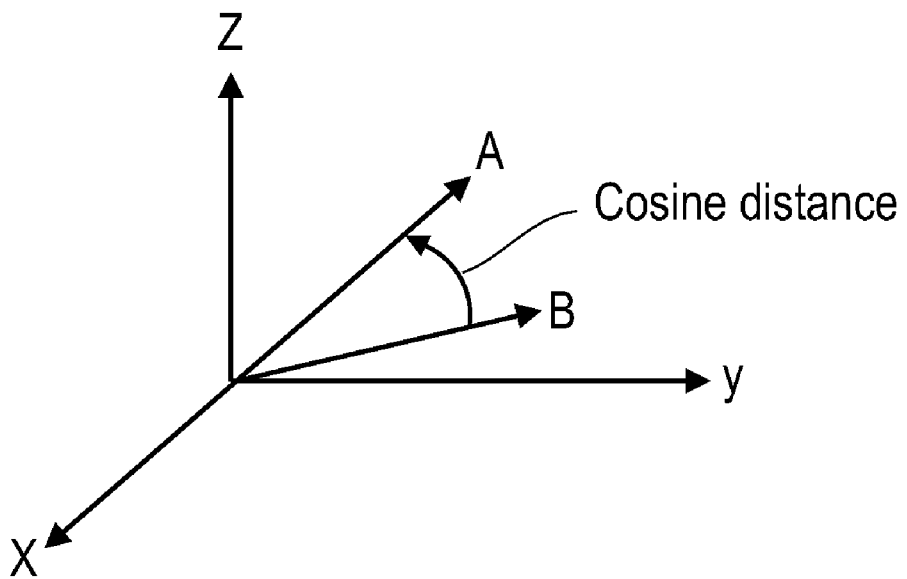
FIG. 10 illustrates schematically how to determine a measure of similarity between two vectors that represent different chemicals.

As indicated by step 330 of FIG. 9, similarity searching is performed on vectors constructed in accordance with the principles outlined in Section 4. One measure of the similarity between two vectors $A=(a_1, a_2, \ldots, a_n)$ and $B=(b_1, b_2, \ldots, b_n)$ is the "cosine distance", which is given by:

$$\text{Similarity } (A,B) = \Sigma(a_j b_j)/(\Sigma a_j a_j)(\Sigma b_j b_j) \quad (3)$$

in which the summations run from 1 to m, where m is the number of dimensions in the vectors. If the number of chemicals being considered is large, m will be correspondingly large and can easily exceed 10,000 or more. For clarity, only 3 dimensions (corresponding to the axes labeled x, y, and z) are shown in FIG. 10, which schematically illustrates the cosine distance between vectors A and B. (Other measures of similarity may be used, such as the Tanimoto coefficient.)

If the vectors A and B represent the same chemical (for example, these vectors are derived from different names for the same compound), then the similarity value will be equal to 1.0. A similarity value of 0.99 would indicate that the molecules in question are similar but not exact, while a value of 0.98 indicates that the molecules are even less similar, and so on. Empirically it has been determined that molecules having a cosine-distance similarity value of less than 0.95 are somewhat different in terms of their chemical functionality.

Figure 11:
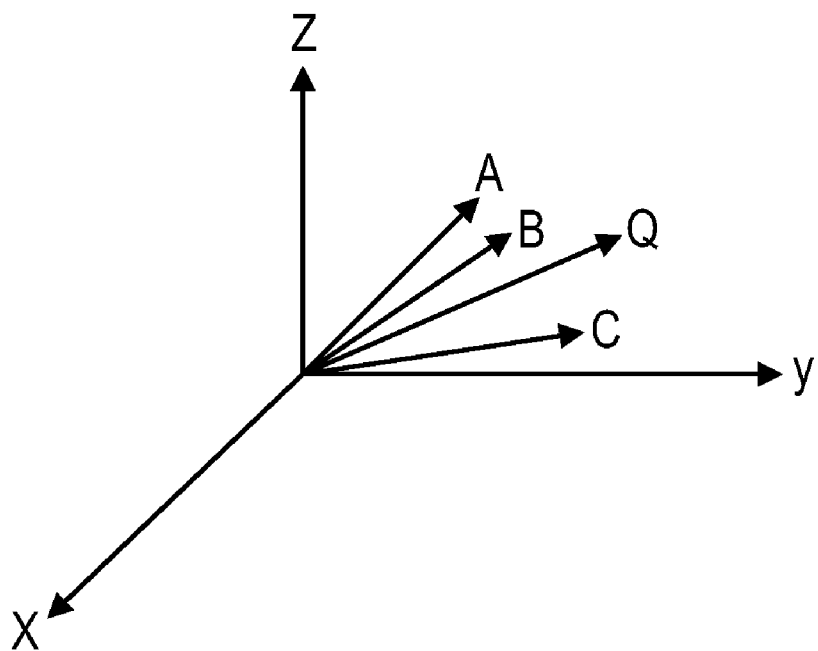
FIG. 11 shows a vector representing a query molecule among a group of vectors representing various chemicals to be searched.
Figure 12:
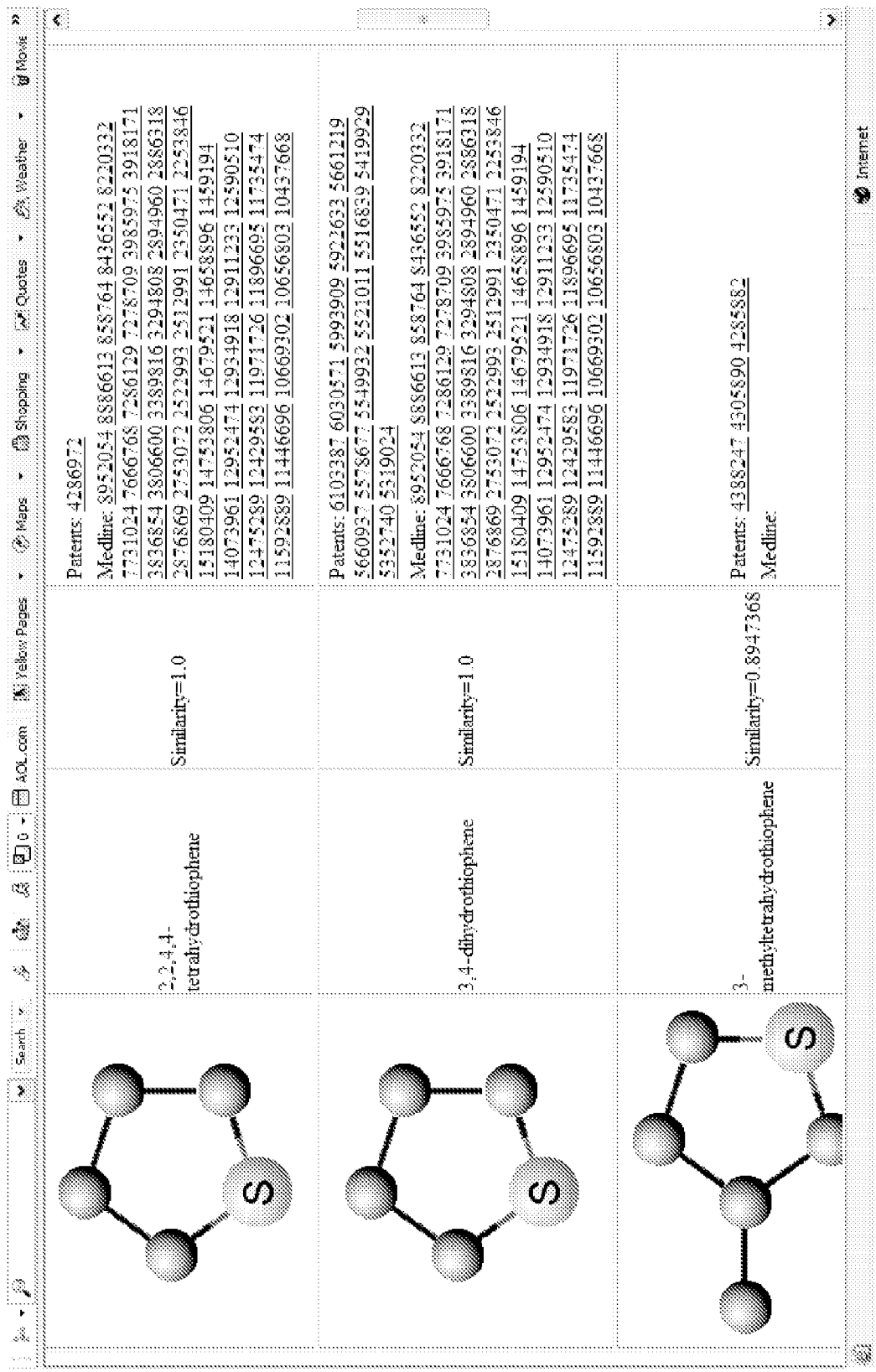
FIG. 12 is a screen shot showing search results that identify different names for the same query molecule and documents corresponding to each of those names.

FIG. 11 illustrates how similarity searching may be performed with respect to a candidate or "query molecule" whose vector is denoted by the letter Q. Vectors C, D, and E are among the vectors that have been constructed from strings corresponding to various molecules. Once again, only 3 dimensions are shown for clarity. In one particular working example of the invention, the query molecule was selected to be tetrahydro-thiophene, and similarity calculations were run against a collection of chemical compounds appearing in a corpus defined by various patents and Medline® references. Representative search results from these calculations are shown in FIG. 12. Note that the formatting shown in this screen shot can be modified to suit user preferences and/or requirements.

For FIG. 12, the starting point for the search was inputting a query molecule into a search program using any one of the many known molecular editors (for example, the Marvin-Sketch software product from ChemAxon Ltd. of Budapest, Hungary, whose web site is given by the concatenation of "www." and "chemaxon." and "com/marvin/"). This was followed by clicking a search button in the program's graphical user interface, which was displayed on a monitor (not shown). The query molecule is shown on the far left hand side of the first row. In this example, each unique chemical name found in the corpus (the patent and Medline® references) has its own row: In each row, the first (i.e., far left hand) column presents a chemical structure corresponding to the unique chemical name given in the second column, the third column gives a similarity value, and the fourth column (the most rightward column) lists all the patents and references containing the chemical name appearing in the second column. The similarity value for each row is calculated between the two vectors corresponding to the query molecule (shown in the first row of the first column) and the chemical name appearing in the second column of that row. Note that the first two rows both show a similarity value of 1.0, since 2,2,4,4-tetrahydrothiophene and 3,4-dihydrothiophene are different names for the same chemical compound. Significantly, this method identifies documents disclosing chemicals identical to the query molecule, even if those documents include different chemical names for the query molecule.

Figure 13:
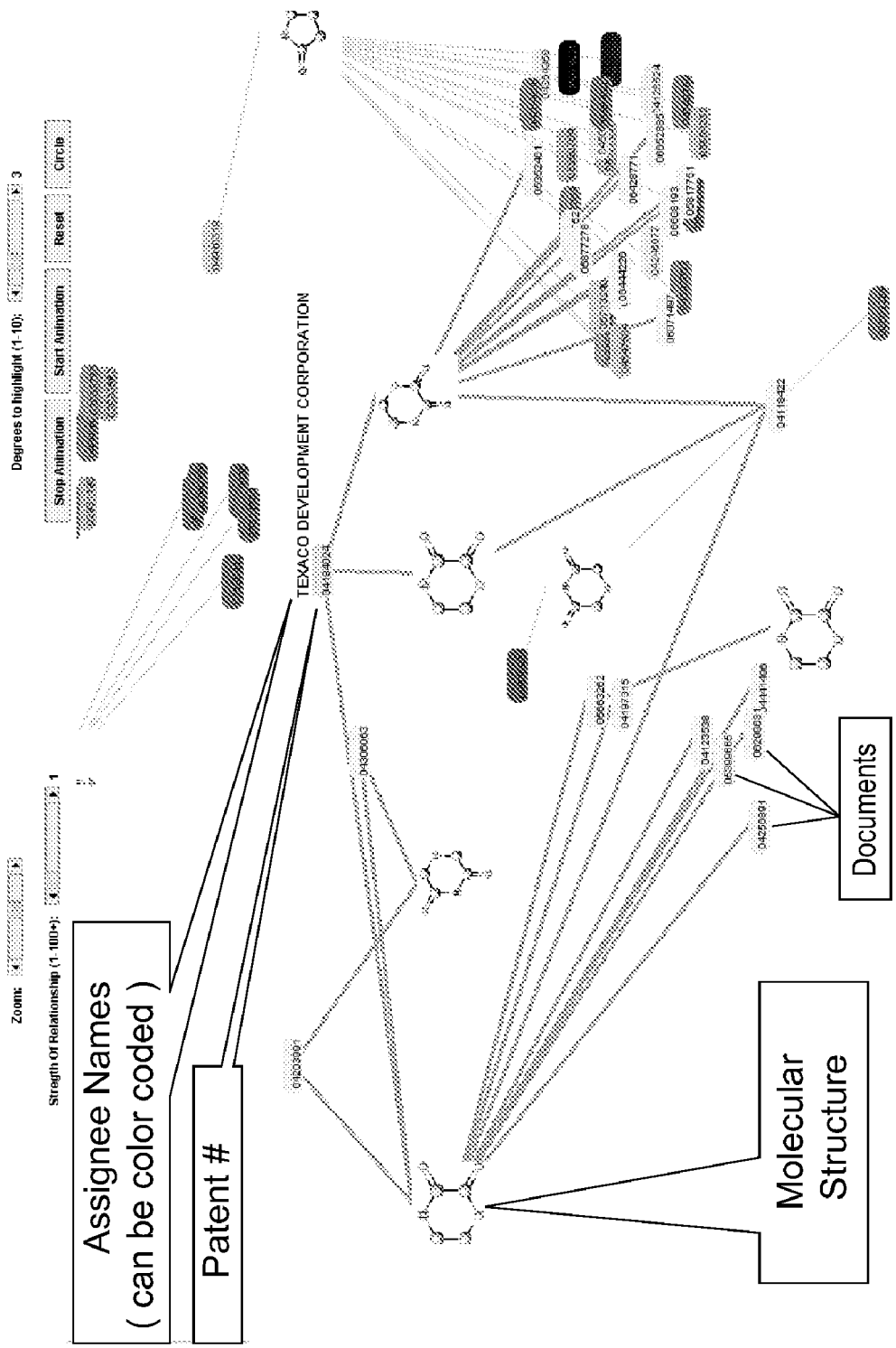
FIG. 13 is a screen shot of certain search results, showing the relationship between certain chemicals and documents in which those chemicals appear.

FIG. 13 shows a screen shot of search results, in which certain molecules of interest are displayed. Several different chemical structures are shown, and line segments connect documents referring to the chemicals of interest. To this end, minimal distance grouping techniques may be employed to adjust the graphical display to fit the available screen space. FIG. 13 provides a visual representation of how a chemical structure may be mentioned in multiple documents, such as patents. The documents are labeled using an appropriate identification or reference number, e.g., a US Patent number. Any patent numbers may be advantageously color coded to reflect the assignee. Alternatively, one may tailor the color coding to reflect the US patent class, subclass, or names of the inventors. Such color coding arrangements allow for easier navigation of the information being presented.

Figure 14:
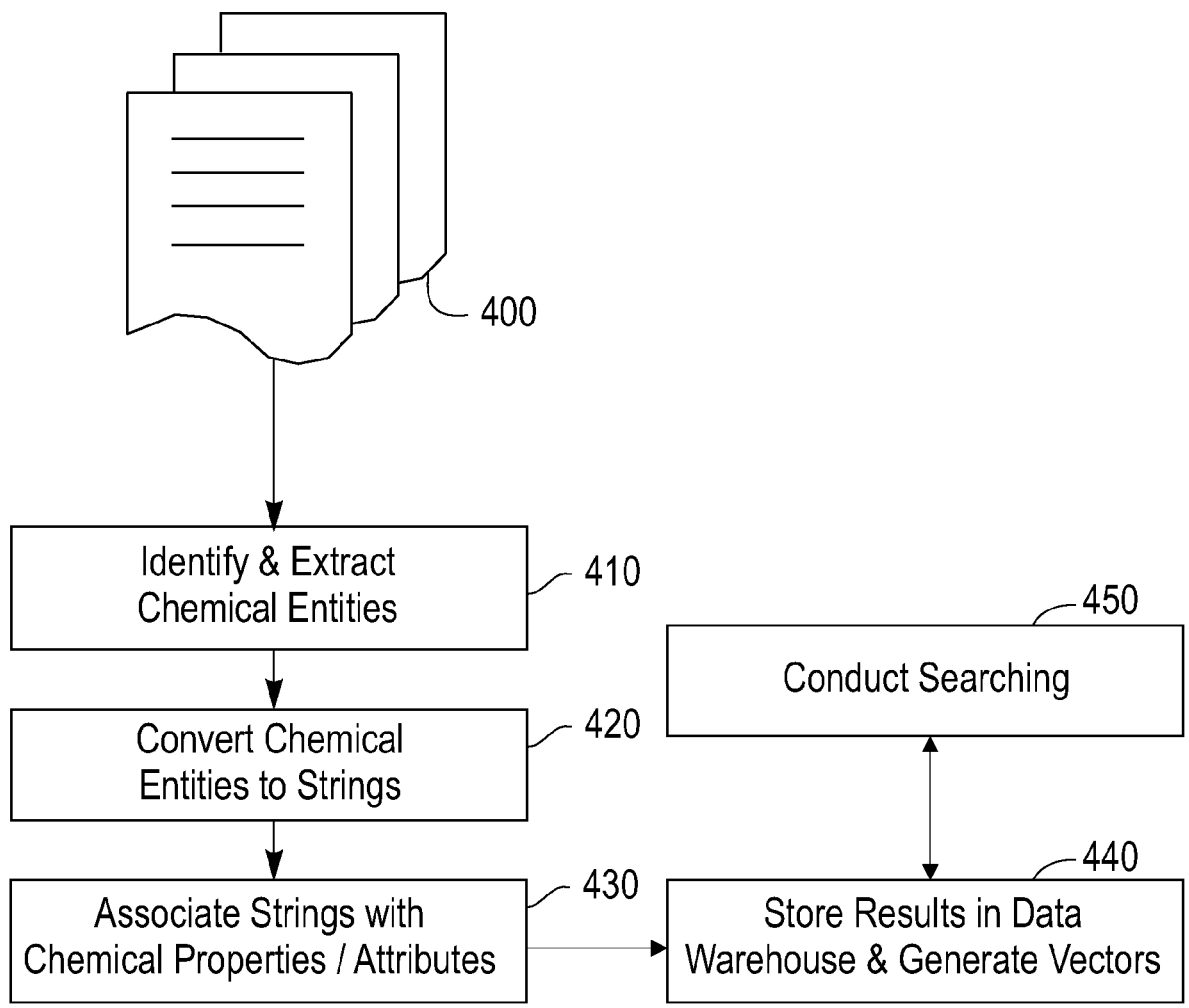
FIG. 14 gives an overview of a method directed to text analytics and annotation techniques.

FIG. 14 gives an overview of a text analytics/annotation process. The documents 400 containing chemical entities may include multi-page documents, such as patents. As noted above in connection with Section 1, text analytics algorithms are used to identify and extract these chemical entities (see also Step 410 of FIG. 14), which may include chemical names, structures, chemical identifier strings, and so on. As indicated in Step 420, a chemical name is processed via one of many available name to structure conversion programs, thereby permitting the chemical entity to be converted into its corresponding InChI string (or another appropriate machine readable chemical identifier representation, such as a SMILES string, SD file, or MOL file). SMILES strings, for example, may be employed in computational calculations and/or as input for other applications (e.g., database applications) to derive attributes or "properties" about the corresponding chemical, as indicated in Step 430. The strings may be linked to properties and attributes of the corresponding chemicals (e.g., these properties and attributes may be stored in a database.)

This process creates chemically related meta-data that in turn can be associated with the documents as "document" metadata, as indicated in Step 440. The chemical names and other entities in the documents can be "annotated" with their respective properties and/or attributes. (Alternatively, the properties and/or attributes may be stored in a database or data warehouse and associated or linked with the corresponding documents.) Once the source document is annotated with these properties, the properties themselves can be used as parameters for enhancing the overall search process. For example, the word "benzene" can be annotated with its boiling point (bp 80.1° C.), toxicity, and/or other properties. Thus, a user can run a query for all solvents having a boiling point in a temperature range that included 80.1° C., thereby identifying documents having the word benzene. Additionally, by indexing and vectorizing the SMILES strings and/or InChI strings as in the present invention, one can use the corresponding chemical vectors as tools for searching and clustering documents containing particular chemical names. Thus, once chemical entities (e.g., names) are converted into respective InChIs (and/or SMILES) strings and subsequently vectorized, documents may be clustered based on the similarity of the chemicals in those documents. Additionally, the chemical identifier strings themselves may include information related to functional properties of the chemical, e.g., the InChI string format may be advantageously extended to include one or more layers dedicated to functional properties (such as boiling point and other physical properties), with these layers then facilitating searches.

In one exemplary implementation of the invention, a system was developed that extracted 65,645,252 chemical names from a corpus of US Patents, with all these names being successfully converted to SMILES strings and/or InChIs. When duplicate chemicals were eliminated, this resulted in a database of ~3,623,248 unique molecular structures. These chemical compounds were then converted into InChI strings. Each compound's InChI representation was vectorized and indexed. Using this index, a user is able to call up a particular compound by drawing a molecule or importing a molecule (e.g., from the Internet or Intranet), and then searching for Patents and Medline® articles containing similar structures.

6. Computing System

Figure 15:
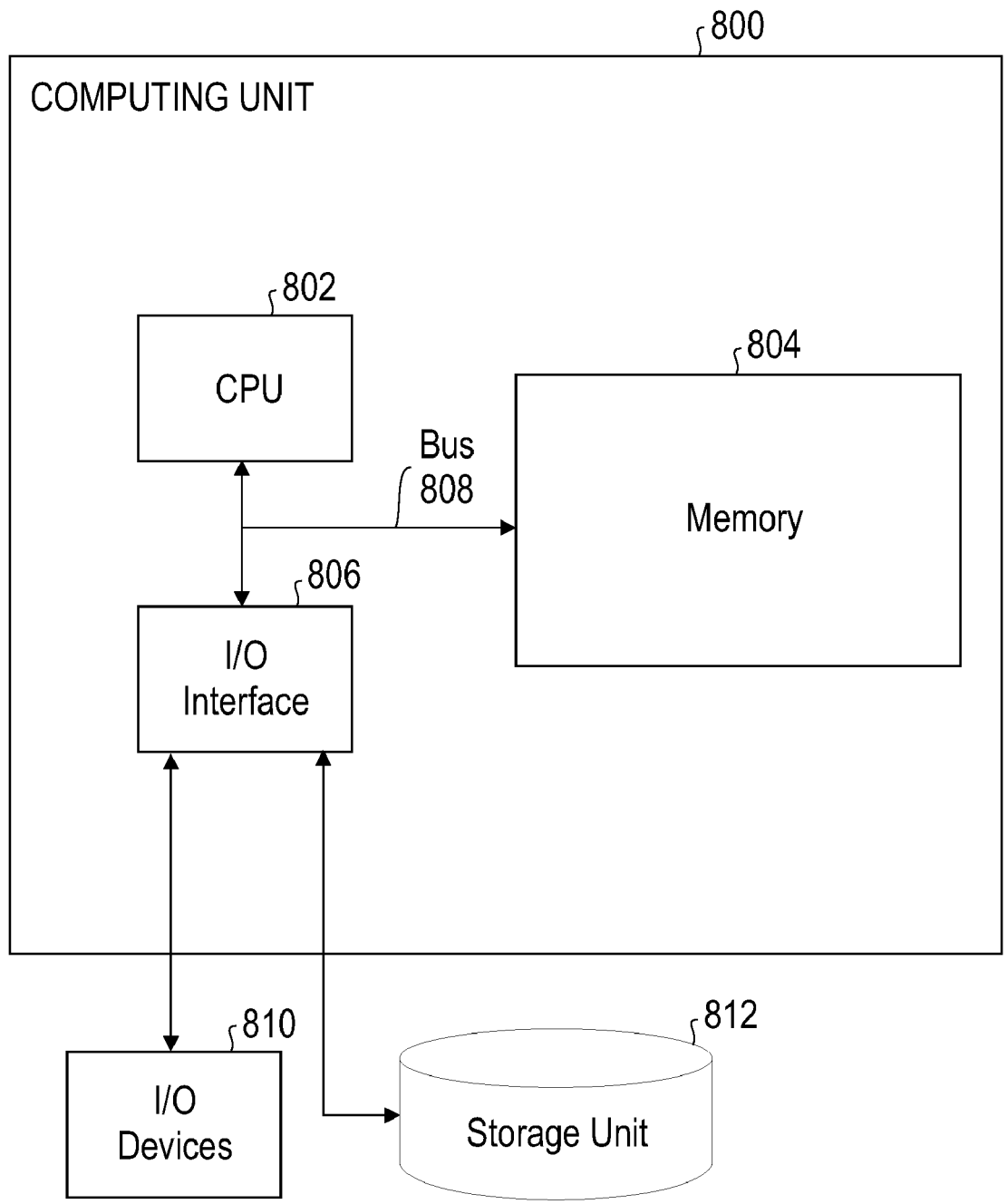
FIG. 15 is a block diagram of a computing unit that may be used in implementing the methods disclosed herein.

FIG. 15 is a block diagram of a computing unit 800 for implementing embodiments of the invention. Computing unit 800 is suitable for storing and/or executing program code directed to implementing the methods disclosed herein, and generally comprises a central processing unit (CPU) 802, a memory 804, an input/output (I/O) interface 806, a bus 808, I/O devices 810 and a storage unit 812. CPU 802 performs computation and control functions of computing unit 800. CPU 802 may comprise a single processing unit, or be distributed across one or more processing units in one or more locations (e.g., on a client and server).

Local memory elements of memory 804 are employed during actual execution of the program code used to implement the methods disclosed herein. Cache memory elements of memory 804 provide temporary storage of at least some program code in order to reduce the number of times code must be retrieved from bulk storage during execution. Further, memory 804 may include other systems not shown in FIG. 15, such as an operating system (e.g., Linux) that runs on CPU 802 and provides control of various components within and/or connected to computing unit 800.

Memory 804 may comprise any known type of data storage and/or transmission media, including bulk storage, magnetic media, optical media, random access memory (RAM), read-only memory (ROM), a data cache, a data object, etc. Storage unit 812 is, for example, a magnetic disk drive or an optical disk drive that stores data. Moreover, like CPU 802, memory 804 may reside at a single physical location, comprising one or more types of data storage, or be distributed across a plurality of physical systems in various forms. Further, memory 804 can include data distributed across, for example, a LAN, WAN or storage area network (SAN) (not shown).

I/O interface 806 comprises any system for exchanging information to or from an external source. I/O devices 810 comprise any known type of external device, including a display monitor, keyboard, mouse, printer, speakers, handheld device, printer, facsimile, etc. Bus 808 provides a communication link between each of the components in computing unit 800, and may comprise any type of transmission link, including electrical, optical, wireless, etc.

I/O interface 806 also allows computing unit 800 to store and retrieve information (e.g., program instructions or data) from an auxiliary storage device (e.g., storage unit 812). The auxiliary storage device may be a non-volatile storage device (e.g., a CD-ROM drive which receives a CD-ROM disk). Computing unit 800 can store and retrieve information from other auxiliary storage devices (not shown), which can include a direct access storage device (DASD) (e.g., hard disk or floppy diskette), a magneto-optical disk drive, a tape drive, or a wireless communication device.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

The invention can take the form of a computer program product accessible from a computer-usable or computer-readable medium providing program code for use by, or in connection with, a computing unit 800 or any instruction execution system to provide and facilitate the capabilities of the present invention. For the purposes of this description, a computer-usable or computer-readable medium can be any apparatus that can contain, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, RAM 804, ROM, a rigid magnetic disk and an optical disk. Current examples of optical disks include compact disk-read-only memory (CD-ROM), compact disk-read/write (CD-R/W) and DVD.

The flow diagrams depicted herein are provided by way of example. There may be variations to these diagrams or the steps (or operations) described herein without departing from the spirit of the invention. For instance, in certain cases, the steps may be performed in differing order, or steps may be added, deleted or modified. All of these variations are considered a part of the present invention as recited in the appended claims.

The invention may be embodied in other specific forms without departing from its spirit or essential characteristics. The described embodiments are to be considered in all respects only as illustrative and not restrictive. The scope of the invention is therefore indicated by the appended claims rather than the foregoing description. All changes within the meaning and range of equivalency of the claims are to be embraced within that scope.

What is claimed is:

1. A method, comprising:
converting chemical names to respective chemical identifier strings, the chemical identifier strings including symbols and having a common format, the chemical identifier strings including strings of differing numbers of symbols;
constructing respective vectors from the chemical identifier strings, the vectors having a common vector space that is based on information extracted from a plurality of the chemical identifier strings, each of the vectors being constructed by comparing information in its corresponding chemical identifier string with the vector space;

storing at least some of the vectors in at least one memory device; and using a computer to search at least some of the stored vectors to identify certain chemical structures that are at least similar to each other.

2. The method of claim 1, wherein the identified chemical structures include structures that are identical to each other.

3. The method of claim 1, wherein the chemical identifier strings are InChI strings.

4. The method of claim 1, further comprising:
extracting chemical names from the text of different documents; and
identifying particular documents from which said certain chemical structures were extracted.

5. The method of claim 4, wherein said particular documents include patents having named assignees and inventors, the method further comprising identifying at least one of the assignees and the inventors.

6. The method of claim 1, wherein a vector corresponding to a query molecule is used to identify said certain chemical structures.

7. The method of claim 1, comprising evaluating at least one of cosine distance calculations and Tanimoto coefficient calculations to identify said certain chemical structures.

8. The method of claim 1, wherein prior to searching, the vectors are normalized to unit vectors.

9. The method of claim 1, wherein at least one million chemical names are converted to the common format.

10. The method of claim 1, wherein the chemical names include IUPAC names, the method further comprising:
converting IUPAC names to respective structures; and
converting said respective structures to respective chemical identifier strings having the common format.

11. The method of claim 1, wherein said respective vectors are constructed by:
extracting sequences of symbols from each of the plurality of chemical identifier strings; and
defining a vector for each of the plurality of the strings, the common vector space including dimensions given by a plurality of the extracted sequences.

12. The method of claim 1, wherein at least some of the chemical names are extracted from at least one document having text that has been tokenized, so that tokens correspond to terms within the document, the method further comprising:
evaluating each token against at least 2 different Markov models to determine respective relative probabilities that the token corresponds to the Markov models, wherein at least one of the Markov models is directed to chemical terms;
for each token, comparing the relative probabilities with each other to determine which Markov model is more likely to be associated with the token; and
identifying tokens most likely to correspond to said at least one Markov model directed to chemical terms, so that chemical terms within the document are identified.

13. The method of claim 1, wherein the stored vectors include sparse vector representations.

14. At least one tangible, non-transitory computer-useable medium, said at least one medium having a computer-readable program, wherein the program upon being processed on a computer causes the computer to implement the steps of:
converting chemical names to chemical identifier strings, the chemical identifier strings including respective symbols and having a common format, the chemical identifier strings including strings of differing numbers of symbols;
constructing respective vectors from the chemical identifier strings, the vectors having a common vector space that is based on information extracted from a plurality of the chemical identifier strings, each of the vectors being constructed by comparing information in its corresponding chemical identifier string with the vector space;
storing at least some of the vectors in at least one memory device; and
searching at least some of the stored vectors to identify certain chemical structures that are at least similar to each other.

15. A method, comprising:
using a computer to extract chemical entities from different documents, the chemical entities including entities having different formats with respect to at least one of name and chemical identifier string;
representing the chemical entities as respective chemical identifier strings having a common format, the chemical identifier strings including strings of differing numbers of symbols;
constructing respective vectors from the commonly formatted chemical identifier strings, the vectors having a common vector space that is based on information extracted from a plurality of the chemical identifier strings, each of the vectors being constructed by comparing information in its corresponding chemical identifier string with the vector space;
storing at least some of the vectors in at least one memory device; and
searching at least some of the stored vectors.

16. The method of claim 15, said step of constructing respective vectors comprising:
extracting sequences of symbols from each of the commonly formatted chemical identifier strings; and
defining a vector for each of the commonly formatted strings, the vectors having a common vector space that includes dimensions given by a plurality of the extracted sequences.

17. The method of claim 16, wherein the commonly formatted strings are InChI strings.

18. The method of claim 16, wherein the commonly formatted strings include information in the InChI format, as well as additional information related to functional properties of the chemical entities, the method further including searching the additional information.

19. The method of claim 15, the chemical entities including chemical names, chemical formula, chemical structures, and chemical identifier strings.

20. The method of claim 15, wherein at least some of the chemical entities are extracted from at least one document having text that has been tokenized, so that tokens correspond to terms within the document, the method further comprising:
evaluating each token against at least 2 different Markov models to determine respective relative probabilities that the token corresponds to the Markov models, wherein at least one of the Markov models is directed to chemical terms;
for each token, comparing the relative probabilities with each other to determine which Markov model is more likely to be associated with the token; and
identifying tokens most likely to correspond to said at least one Markov model directed to chemical terms, so that chemical terms within the document are identified.

21. At least one tangible, non-transitory computer-useable medium, said at least one medium having a computer-readable program, wherein the program upon being processed on a computer causes the computer to implement the steps of:
- extracting chemical entities from different documents, the chemical entities including entities having different formats with respect to at least one of name and chemical identifier string;
- representing the chemical entities as respective chemical identifier strings having a common format, the chemical identifier strings including strings of differing numbers of symbols;
- constructing respective vectors from the commonly formatted chemical identifier strings, the vectors having a common vector space that is based on information extracted from a plurality of the chemical identifier strings, each of the vectors being constructed by comparing information in its corresponding chemical identifier string with the vector space;
- storing at least some of the vectors in at least one memory device; and
- searching at least some of the stored vectors.

22. A system, comprising:
said at least one medium of claim 21; and
a processor in communication with said at least one medium, the processor and said at least one medium together forming at least part of a computer system.

23. A computer-implemented method, comprising:
processing the program of said at least one medium of claim 21 to implement the steps of claim 21; and
delivering to a client output resulting from implementing the steps of claim 21.

24. The method of claim 11, wherein the plurality of sequences are extracted from InChI strings.

25. The method of claim 11, wherein the plurality of sequences include consecutive symbols containing carbon connectivity information.

26. The method of claim 25, wherein the plurality of sequences that include consecutive symbols include every possible sequence that has no greater than a predetermined number of symbols.

27. The method of claim 11, wherein the plurality of sequences include consecutive symbols containing hydrogen connectivity information.

28. The method of claim 11, wherein each of the plurality of sequences has no greater than a predetermined number of symbols.

29. The method of claim 11, wherein the vector space includes dimensions defined by information taken from chemical formulae of the chemicals.

30. The method of claim 29, wherein the dimensions of the vector space include dimensions defined by elements of the chemical formulae.

* * * * *